United States Patent
Lucas

(10) Patent No.: US 9,730,768 B2
(45) Date of Patent: Aug. 15, 2017

(54) CAD-CAM AGP SPLINT—A METHOD OF AUTOMATICALLY PRODUCING OR REPRODUCING A CUSTOMIZED AGP (ANTERIOR GUIDANCE PACKAGE) EQUIPPED SPLINT FOR A PATIENT WITH/WITHOUT A SEVERE MALOCCLUSION VIA ONE TIME DENTIST VISIT

(71) Applicant: Kelly Lucas, Wasilla, AK (US)

(72) Inventor: Kelly Lucas, Wasilla, AK (US)

(*) Notice: Subject to any disclaimer, the term of this patent is extended or adjusted under 35 U.S.C. 154(b) by 785 days.

(21) Appl. No.: 13/918,754

(22) Filed: Jun. 14, 2013

(65) Prior Publication Data

US 2014/0370465 A1    Dec. 18, 2014

Related U.S. Application Data

(63) Continuation-in-part of application No. 13/774,920, filed on Feb. 22, 2013, now Pat. No. 9,526,590.

(51) Int. Cl.
*A61C 9/00* (2006.01)
*A61C 5/00* (2017.01)
*A61C 7/36* (2006.01)

(52) U.S. Cl.
CPC ............... *A61C 5/007* (2013.01); *A61C 7/36* (2013.01)

(58) Field of Classification Search
CPC ......... A61C 9/00; A61C 9/0006; A61C 9/004; A61C 5/007; A61C 7/08; A61C 7/36
USPC .............. 433/213–215, 54–67; 128/859–861
See application file for complete search history.

(56) References Cited

U.S. PATENT DOCUMENTS

| | | | |
|---|---|---|---|
| 2,529,429 A | 11/1950 | Spiro | |
| 4,773,854 A | 9/1988 | Weber | |
| 4,901,737 A | 2/1990 | Toone | |
| 5,059,120 A | 10/1991 | Lee | |
| 5,085,584 A | 2/1992 | Boyd | |
| 5,203,701 A * | 4/1993 | Burtch | A61F 5/01 433/215 |
| 5,365,945 A | 11/1994 | Halstrom | |

(Continued)

FOREIGN PATENT DOCUMENTS

EP      0312368      4/1989

OTHER PUBLICATIONS

Laura Maestre-Ferrin, et al.,"Virtual articulator for the analysis of dental occlusion: An update", Med Oral Patol Oral Cir Bucal. vol. 17(1): e160-e163, Jan. 2012.

(Continued)

*Primary Examiner* — Yogesh Patel
(74) *Attorney, Agent, or Firm* — Troutman Sanders LLP; Ryan A. Schneider; Dustin B. Weeks

(57) ABSTRACT

A method of automatically producing or reproducing a customized AGP (Anterior Guidance Package) equipped splint for a patient with or without a severe malocclusion is provided. The method of automatically producing or reproducing an AGP equipped splint according to current invention comprises of combining Virtual Articulation, CAD (Computer Aided Design)-CAM (Computer Aided Manufacturing) method with AGP and special retentive piece technology. The method of the current invention enables a patient with or without a severe malocclusion to receive his/her customized AGP equipped splint or a replacement thereof automatically without visiting the dentist again and again.

16 Claims, 19 Drawing Sheets

(56) References Cited

U.S. PATENT DOCUMENTS

| | | |
|---|---|---|
| 5,427,117 A | 6/1995 | Thornton |
| 5,722,828 A | 3/1998 | Halstrom |
| 5,795,150 A | 8/1998 | Boyd |
| 5,868,138 A | 2/1999 | Halstrom |
| 6,041,784 A | 3/2000 | Halstrom |
| 6,161,542 A | 12/2000 | Halstrom |
| 6,431,871 B1 * | 8/2002 | Luthardt ............ A61C 13/0004 433/223 |
| 6,666,212 B2 | 12/2003 | Boyd, Sr. |
| 6,886,566 B2 | 5/2005 | Eubank |
| 7,556,044 B2 | 7/2009 | Ball |
| 7,654,267 B2 | 2/2010 | Boyd |
| 8,156,940 B2 | 4/2012 | Lee |
| 2002/0000230 A1 | 1/2002 | Gaskell |
| 2004/0172150 A1 * | 9/2004 | Perot .................. A61C 13/0004 700/98 |
| 2005/0288624 A1 | 12/2005 | Boyd |
| 2007/0079833 A1 | 4/2007 | Lamberg |
| 2007/0099144 A1 | 5/2007 | Keski-Nisula |
| 2007/0178420 A1 | 8/2007 | Keski-Nisula et al. |
| 2008/0000483 A1 | 1/2008 | Halstrom |
| 2008/0090201 A1 * | 4/2008 | Andrews ................ A61C 11/02 433/60 |
| 2008/0099029 A1 | 5/2008 | Lamberg |
| 2009/0280451 A1 * | 11/2009 | Perot ...................... A61C 11/00 433/62 |
| 2009/0325121 A1 * | 12/2009 | Ragade ................ A61C 11/022 433/57 |
| 2010/0147315 A1 | 6/2010 | Chodorow |
| 2010/0279246 A1 | 11/2010 | Keski-Nisula et al. |
| 2011/0030704 A1 | 2/2011 | Hanna |
| 2011/0114100 A1 | 5/2011 | Alvarez |
| 2011/0132380 A1 * | 6/2011 | Goldsby .................. A61B 1/24 128/861 |
| 2011/0139162 A1 | 6/2011 | Chodorow |
| 2011/0308532 A1 | 12/2011 | Nelissen |
| 2012/0266896 A1 | 10/2012 | Chodorow |
| 2012/0266897 A1 | 10/2012 | Chodorow |
| 2012/0272972 A1 | 11/2012 | Chodorow |
| 2013/0098375 A1 | 4/2013 | Urbansk |
| 2013/0146067 A1 | 6/2013 | Tschackert |
| 2015/0019176 A1 * | 1/2015 | Presswood ........... A61C 9/0053 703/1 |

OTHER PUBLICATIONS

E. Solaberrieta, et al.,"Design of a Virtual Articulator for the Simulation and Analysis of Mandibular Moments in Dental CAD/CAM", Proceedings of the 19th CIRP Design Conference-Competitive design, pp. 323, 30-31, Mar. 2009.

Frank, et al.,"Great Lakes Dightal Splint", http://www.greatlakesortho.com/resource-center/digital-splints-users-group.

Laura Maestre-Ferrin, et al., "Virtual articulator for the analysis of dental occlusion: An update," Med Oral Patol Oral Cir Bucal. vol. 17(1): e160-a163, Jan. 2012.

E. Solaberrieta, et al., "Design of a Virtual Articulator for the Simulation and Analysis of Mandibular Moments in Dental CAD/CAM," Proceedings of the 19th CIRP Design Conference-Competitive Design, pp. 323, 30-31, Mar. 2009.

Frank, et al., "Great Lakes Digital Splint," http://www.greatlakesortho.com/resource-center/digital-splints-users-group.

www.chairsidesplint.com—NTI-tss devies, accessed May 19, 2015.

Spear, Dr. Frank M., et al., "Great Lakes Splint Appliance Selection Guide" accessed on May 19, 2015, http://www.greatlakesortho.com/content/files/resources/SplintApplianceSelectionGuide_S222.pdf.

* cited by examiner

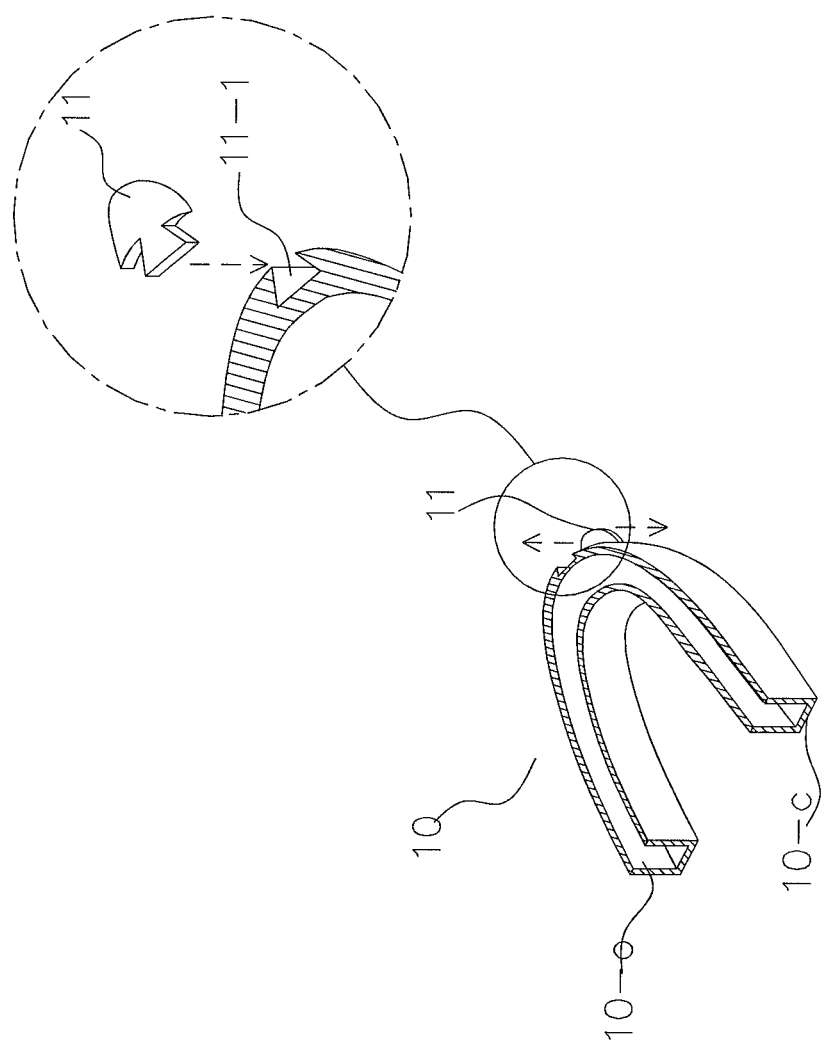
FIG. 5-a

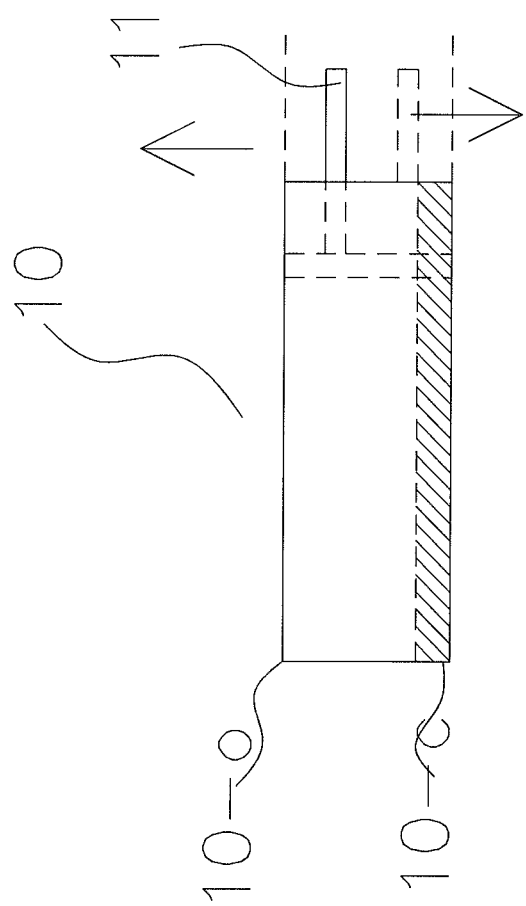
FIG. 5-b

CAD-CAM AGP SPLINT—A METHOD OF AUTOMATICALLY PRODUCING OR REPRODUCING A CUSTOMIZED AGP (ANTERIOR GUIDANCE PACKAGE) EQUIPPED SPLINT FOR A PATIENT WITH/WITHOUT A SEVERE MALOCCLUSION VIA ONE TIME DENTIST VISIT

CROSS-REFERENCE TO RELATED APPLICATIONS

This application is a continuation-in-part to U.S. patent application No. 13/774,920, filed 22 Feb. 2013, now U.S. Pat. No. 9,526,590, issued on 27 Dec. 2016.

FIELD OF THE INVENTION

Current invention relates a method of producing or reproducing an AGP (Anterior Guidance Package) equipped splint, especially relates to a method of automatically producing or reproducing a customized AGP equipped splint for a patient with or without a severe malocclusion.

BACKGROUND OF THE INVENTION

An AGP (Anterior Guidance Package) equipped splint has a unique ability to provide guidance anterior to the teeth therefore enhancing the mechanical advantage over the muscles of mastication. The AGP equipped splint uniquely provides true anterior guidance to the jaw and the elimination of posterior interferences (collisions) without any limitations due to the conditions of, malocclusion of, or even the presence (or not) of the anterior teeth. The AGP equipped splint uniquely provides this guidance to the jaw with a minimal vertical dimension penalty when the jaw is in centric relation because the AGP can be placed anterior to and independent of teeth. The AGP equipped splint gives unprecedented control of the anterior guidance and limitations of the jaw to the operator because the selection of guidance, or design of that guidance, by the operator is unlimited and independent of teeth. The AGP splint introduced by the current applicant disclosed a facilitated use of the AGP for the direct fabrication of an AGP splint that provides anterior guidance anterior to any limitations of teeth achieved easier, less expensively, with minimal vertical dimension increase, unprecedented control over the design of the anterior guidance, and a greater mechanical advantage over the muscles of mastication as compared to any previous night guard system. However, the patient must spend additional time in a dentist office to get a new AGP splint when it is worn out or damaged. It is the purpose of the current application to provide a method that minimizes the time and effort of both the patient and the dentist to get a new AGP splint specially designed for her/him. The CAD-CAM AGP splint according to current invention provides another unique benefit of the AGP package. Using a virtual articulator and CAD-CAM technology the AGP splint can be produced to give the patient any set of guidance parameters the operator deems appropriate. Digital records made or traditional records converted to digital made from the patient can be analyzed and then taking advantage of the flexibility of the AGP, an infinite number of design possibilities dependent upon the operators' goals for that patient can be realized. One could produce a superior, seamless AGP splint for the bruxism patient, or a sophisticated AGP TMD (Temporo-Mandibular Disorders) splint produced with specific jaw repositioning and guidance limitations as proscribed by the operator.

DESCRIPTION OF PRIOR ARTS

Laura Maestre-Ferrín, et al. reviewed Virtual articulator development for the analysis of dental occlusion on Med Oral Patol Oral Cir Bucal. 2012 January; 17(1): e160-e163. Published online 2011 Dec. 6. doi: 10.4317/medoral.17147 PMCID: PMC3448198. According to them the virtual articulator can simulate the specific masticatory movement of the patient. During mandibular animation, the program calculates the sites where the opposing teeth come into contact.

E. Solaberrieta, et al. introduced a method of designing dental prostheses, adding kinematic analysis to the design process on Proceedings of the $19^{th}$ CIRP Design Conference-Competitive design, pp 323, 30-31, Mar. 2009. The method comprises of 1) scanning plaster models, 2) select type of articulator, 3) statically model the prosthesis, 4) simulate the excursive movements using a CAD system, analyzing occlusal collisions to modify the design. However, this method does not provide how to reproduce a customized Anterior Guidance Package equipped splint automatically.

U.S. Patent Application Publication 20100279246, 20070178420, 20070099144 by Keski-Nisula; Katri; et al. disclose an odontological device and device series to guide an individual's occlusion and a method to be used in selecting an occlusion guidance appliance device to be used in orthodontic treatment. This kind of device contains a U-shaped arch with a lower surface on the side of the lower jaw and a higher surface on the side of the upper jaw, and in both of which there are concaves in which to place the individual's teeth, and where the bottoms of the concaves form of the isthmus separating the concaves from one another.

U.S. Patent Application Publication 20080000483, U.S. Pat. Nos. 6,161,542, 6,041,784, and U.S. Pat. No. 5,365,945 to Halstrom disclosed an intra-oral dental appliance for treatment of sleep disorders including snoring, sleep apnea and nocturnal bruxism. The appliance includes an upper member conforming to the patient's maxillary dentition; a lower member conforming to the patient's mandibular dentition; and a connecting assembly for adjustable coupling of the upper and lower members together. The only benefit in regard to bruxism is that Halstrom's appliance does separate teeth therefore damage to teeth would be eliminated. However, his connecting assembly limits the movement of the jaw. This may cause many problems because the major goal of treatment for tooth damage, myofacial pain, migraines etc. secondary to bruxism, is to allow the jaw (mandible) freedom to relax to its most comfortable position. This position would be centric relation for 99% of people. Centric relation allows the jaw to be in its most anatomically correct stress bearing position and the place where the muscles are most calm. Dentists use centric relation or an even more refined point to create a night guard that allows the mandible to rest there and then guidance from that position to avoid posterior interferences and in contrast to Halstroms' appliance provides freedom so the jaw can move, the patient can yawn, open, sneeze, breathe, swallow etc. normally.

When a person, having a malocclusion, maximally intercuspates their teeth as in bruxism, the jaw is forced to adapt a position other than centric relation. Because of muscle engrams the jaw ends up living in this inappropriate position. Secondly, by locking the lower jaw forward in relation to the upper jaw over time, which will happen when a person wears Halstrom's appliance, the person may experience unintended and inappropriate orthodontic movement of the teeth that create or make worse a malocclusion. Third, by locking the lower jaw forward in relation to the upper jaw you have pulled the mandibular condyle down the articular imminence to a very inappropriate position (not in the fossa). It may prevent damage to teeth but if the person exerts muscle activity in that position, one is more likely to damage the TMJ (Temporomandibular Joint). One major purpose of a night guard is to allow the persons jaw to assume the position of centric relation, not purposely pull the jaw into some other position. Myofacial pain would be terrible for a person wearing this type appliance since the condyles and muscles of mastication are artificially pulled into very inappropriate positions.

U.S. Patent Application Publication 2005028862S., U.S. Pat. No. 7,654,267, U.S. Pat. No. 5,795,150, and U.S. Pat. No. 5,085,584 by Boyd, and U.S. Pat. No. 6,666,212 to Boyd. Sr., illustrate an intraoral discluder for preventing chronic tension headaches, common migraine headaches, and temporo-mandibular disorders that are caused or perpetuated by chronic activity of the temporalis muscle. The discluder includes a trough, contoured to encompass at least one maxillary or mandibular incisor, from which extends a protruding platform, for engagement by the opposing incisors. The trough can be retained on the teeth by any adaptable material than can flow around the teeth and then maintain its shape. Once in place in the wearer's mouth, one or two opposing incisors will come into contact with the platform prior to the upper and lower posterior and/or canine teeth coming into contact, regardless of the position of the mandible, thereby reducing the intensity of the activity of the temporalis muscle. In addition, a special post on the discluder's platform is engageable directly with one or more opposing incisors, to act as a stop and thereby inhibit excessive retrusive movement of the mandible and urge the mandible toward a more protrusive position. This can reduce the intensity of undesired clenching, and it can enhance the size of the wearer's pharyngeal airspace, thereby reducing the incidence and severity of snoring.

However, Boyd's invention did not consider patients who have severe malocclusions, loss of teeth, and periodontally weakened teeth, etc. If a patient with such abnormalities wears Boyd's intraoral discluder and brux while sleeping, it will make the patient's abnormalities worse. Also, as compared to the AGP combined with the special tray of current application, the vertical dimension increase of Boyds device to overcome posterior interferences quickly becomes excessive to the point the patient may not be able to wear it. Also, in Boyds device anterior disclusion is tied to the position of teeth in contrast to the AGP and the current application, which allows not just disclusion, but true guidance, independent of the position of the patients' teeth.

U.S. Pat. No. 4,773,854 to Weber disclosed herein is a device for the representation of condylar movements of a patient and their correct simulation which includes models of sets of teeth to determine the required corrections to the biting surfaces in order to obtain ideal occlusion. The device includes an articulator with the lower part thereof able to be brought into a predetermined three-dimensional relation with respect to an upper part of the articulator and having two blocks having guide elements on the lower part of the articulator to support condyle balls of the upper part of the articulator. The device further includes a lower jaw recording bow and an upper jaw recording bow which can be brought into an active and predetermined relation with respect to the articulator and which disposes of at least three recording plates with corresponding recording pins as well as positioning spoons for the combination of a lower jaw dentition model. With this device, opening movements of articulation may be recorded three-dimensionally so that three clear crossing points are created for the occlusion.

U.S. Pat. No. 4,901,737 to Toone discloses an intra-oral appliance for reducing snoring, which repositions the mandible in an inferior (open) and anterior (protrusive) position as compared to the normally closed position of the jaw. Once the dentist or physician determines the operative "snore reduction position" for a particular patient, an appropriate mold is taken of the maxillary dentition and of the mandibular dentition for formation of the appliance template. The Toone appliance includes a pair of V-shaped spacer members formed from dental acrylic, which extend between the maxillary and mandibular dentition to form a unitary mouthpiece. In an alternative embodiment of the Toone invention, the spacer members are formed in two pieces and a threaded rod is provided to enable adjustment of the degree of mandibular protrusion or retrusion after the mouthpiece is formed.

European patent publication No. 0,312,368 B1 published also discloses an intra-oral device for preventing snoring. This device consists of a U-shaped mouthpiece, which conforms to the upper dental arch of the user and includes a sloped, lower ramp for engaging the mandibular dentition. Normal mouth motions, such as the clenching of the jaw, will cause some of the mandibular dentition to engage the underside of the ramp, thereby camming the lower jaw forward to increase the spacing between the base of the tongue and the posterior wall of the pharynx.

U.S. Pat. No. 5,722,828 to Halstrom discloses an apparatus and method for producing a gothic arch tracing representative of the natural range of motion of a patient's mandible. The apparatus consists of a kit including a mandibular bite rim having a tracing plate; a maxillary bite rim having a tracing arm; and a stylus reversibly connectable to the tracing arm for extending between the tracing arm and the tracing plate externally of the patient's mouth. The stylus has a marker on one end thereof for drawing a gothic arch tracing on a removable paper substrate, such as a post-it note, attachable to the tracing plate. The tracing is used in the fabrication of a dental bite registration mold for the patient. The mold may in turn be used to mount casts of the patient's dentition in a specific relationship as required for prosthetic or therapeutic purposes.

Frank et al, disclosed a full contact splint with anterior guidance on the internet at address http://www.greatlakesortho.com/resource-center/digital-splints-users-group The full contact splint with anterior guidance is to form an anterior guidance under the lower surface of the maxillary retentive piece. However, developing anterior guidance directly to the lower surface of the maxillary retentive piece may or may not be practical dependent upon the position, condition, presence or absence of mandibular anterior teeth and is expensive for both the dentist and patient.

From the above prior arts, it is found that none of the prior art provides an economical, easy to apply and medically safe anterior guidance splint (night guard) for patients as provided by the special retention piece of current application combined with an AGP, to include patients without malocclusion, open bite, deep bite, cross bite, and severe Class II or Class III malocclusions. Also, no prior art provides for anterior guidance that is not tied to and dependent upon the position of anterior teeth. In contrast to all prior arts, the AGP combined with the special retention piece of the current application can provide a splint (night guard) with optimal anterior guidance, which eliminates all posterior interferences with minimal vertical dimension penalty at rest, and can be located ANTERIOR to any limitations of teeth therefore increasing the mechanical advantage of that guidance over the muscles of mastication.

Moreover, none of the prior art provides a method of automatically producing or reproducing a customized AGP equipped splint for a dental patient with or without severe malocclusion.

SUMMARY OF THE INVENTION

An AGP (Anterior Guidance Package) splint, Anterior Guidance Package equipped splint, has a unique ability to provide guidance anterior to the teeth therefore enhancing the mechanical advantage over the muscles of mastication. The AGP equipped splint uniquely provides true anterior guidance to the jaw and the elimination of posterior interferences (collisions) without any limitations due to the conditions of, malocclusion of, or even the presence (or not) of the anterior teeth. The AGP equipped splint uniquely provides this guidance to the jaw with a minimal vertical dimension penalty when the jaw is in centric relation because the AGP can be placed anterior to and independent of teeth. The AGP equipped splint gives unprecedented control of the anterior guidance and limitations of the jaw to the operator because the selection of guidance, or design of that guidance, by the operator is unlimited and independent of teeth. The AGP splint introduced in a series of previous U.S. patent application Ser. No. 13/573,283 and Ser. No. 13/774,920 by the current applicant disclosed a facilitated use of the AGP for the direct fabrication of an AGP splint that provides anterior guidance anterior to any limitations of teeth accomplishing that easier, less expensively, with minimal vertical dimension increase at rest, unprecedented control over the design of the anterior guidance and a greater mechanical advantage over the muscles of mastication as compared to any previous night guard system. However, the patient must spend additional time in a dentist office to get a new AGP splint when it is worn out or damaged. It is the purpose of the current application to provide a method that minimizes the time and effort of both the patient and the dentist to get a new AGP splint specially designed for her/him. The CAD-CAM AGP splint according to current invention provides another unique benefit of the AGP package. Using a virtual articulator and CAD-CAM technology the AGP splint can be produced to give the patient any set of guidance parameters the operator deems appropriate. Digital records made or traditional records converted to digital made from the patient can be analyzed and then taking advantage of the flexibility of the AGP, an infinite number of design possibilities dependent upon the operators' goals for that patient can be realized. One could produce a superior, seamless AGP splint for the bruxism patient, or a sophisticated AGP TMD (Temporo-Mandibular Disorder) splint produced with specific jaw repositioning and guidance limitations as proscribed by the operator. A method of automatically producing or reproducing a customized AGP (Anterior Guidance Package) equipped splint for a patient with or without a severe malocclusion is provided. The method of automatic producing or reproducing an AGP equipped splint according to current invention comprises of combining Virtual Articulation technology, CAD (Computer Aided Design)-CAM (Computer Aided Manufacturing) method with the unique attributes of the AGP and special retentive piece technology. The method of the current invention enables a patient with or without a severe malocclusion to receive his/her customized AGP equipped splint automatically without visiting the dentist again and again.

The method introduced in the current application can be applied to a wide range of stock AGPs, and/or a custom designed AGP for a specific patient. The AGP could have any size or shape to address a very wide range of problems or malocclusions. The maxillary component and/or the mandibular component of the AGP can be designed or modified to any shape or size either individually or as a group to achieve whatever effect the operator desires. For instance, a TMD (TemporoMandibularDisorders) therapist will have available to her/him an unprecedented range of options regarding both limits and guidance to the mandible. In contrast to other systems, the AGP can provide unlimited true anterior guidance, and limits to the mandible independent of the condition, position, presence or absence of teeth. Also uniquely attributable to the AGP, the position of the AGP (and therefore guidance and limits of the mandible) within the AGP splint can be controlled to maximize or minimize different properties of the AGP splint. Considering the unlimited design potential of the AGP, and the extreme flexibility regarding the position of the AGP within the AGP splint, the AGP CAD-CAM splint, and the AGP CAD-CAM TMD splint are far superior to any night guard or TMD appliance system in existence today.

BRIEF DESCRIPTION OF DRAWINGS

FIG. 5-*a* is a perspective view of the special retention piece to receive the AGP.

FIG. 5-*b* is a side view of the special retention piece to receive the AGP.

DETAILED DESCRIPTION OF THE PREFERRED EMBODIMENT

Figure 1:
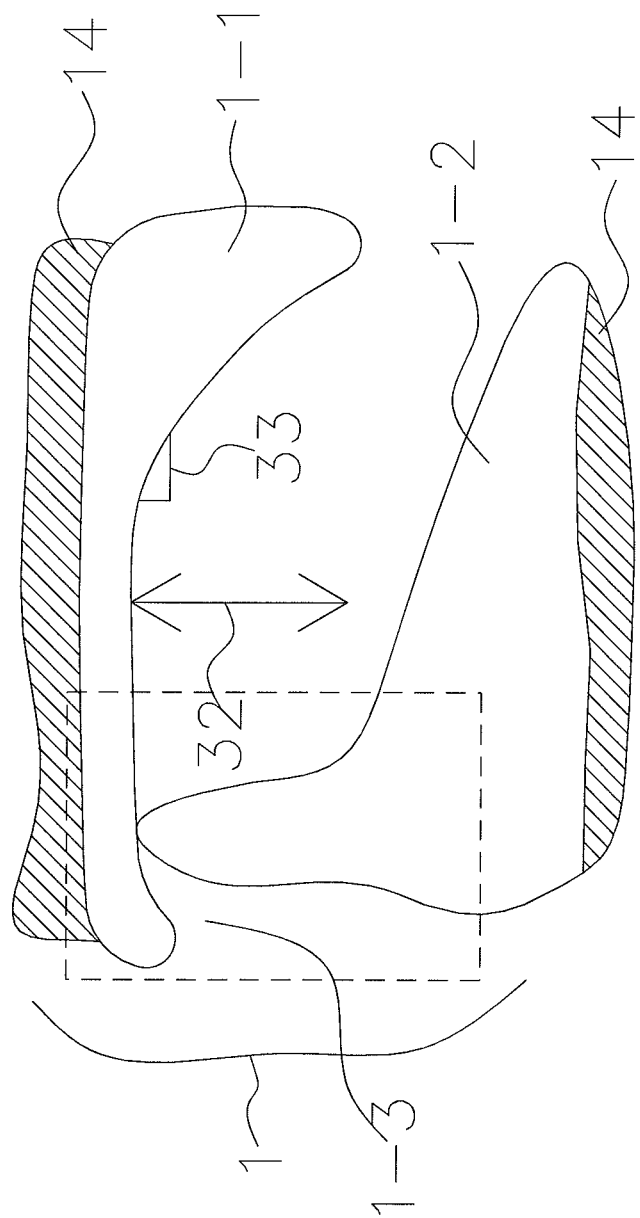
FIG. 1 is a side view of an AGP (Anterior Guidance Package) for the amelioration of the damage and pain caused by bruxism.

FIG. 1 is a side view of an AGP (Anterior Guidance Package) kit (1) for the amelioration of the damage and pain caused by bruxism. The AGP kit (1) could be delivered from the manufacturer already attached to a retentive piece for one arch (maxillary or mandibular arch) and then indexed onto a retentive piece molded to the other arch, or the AGP kit (1) could be indexed by the dentist onto the shelf or shelves of the special retention piece or pieces. The AGP splint kit (1) is comprised of a maxillary guidance component (1-1), a mandibular guidance component (1-2) and a holder (1-3) that temporarily holds the two components (1-1) and (1-2) together in their appropriate (centric relation) position to each other. When the holder (1-3) is removed from the AGP kit (1), the functional parts are named as AGP (12).

Figure 2:
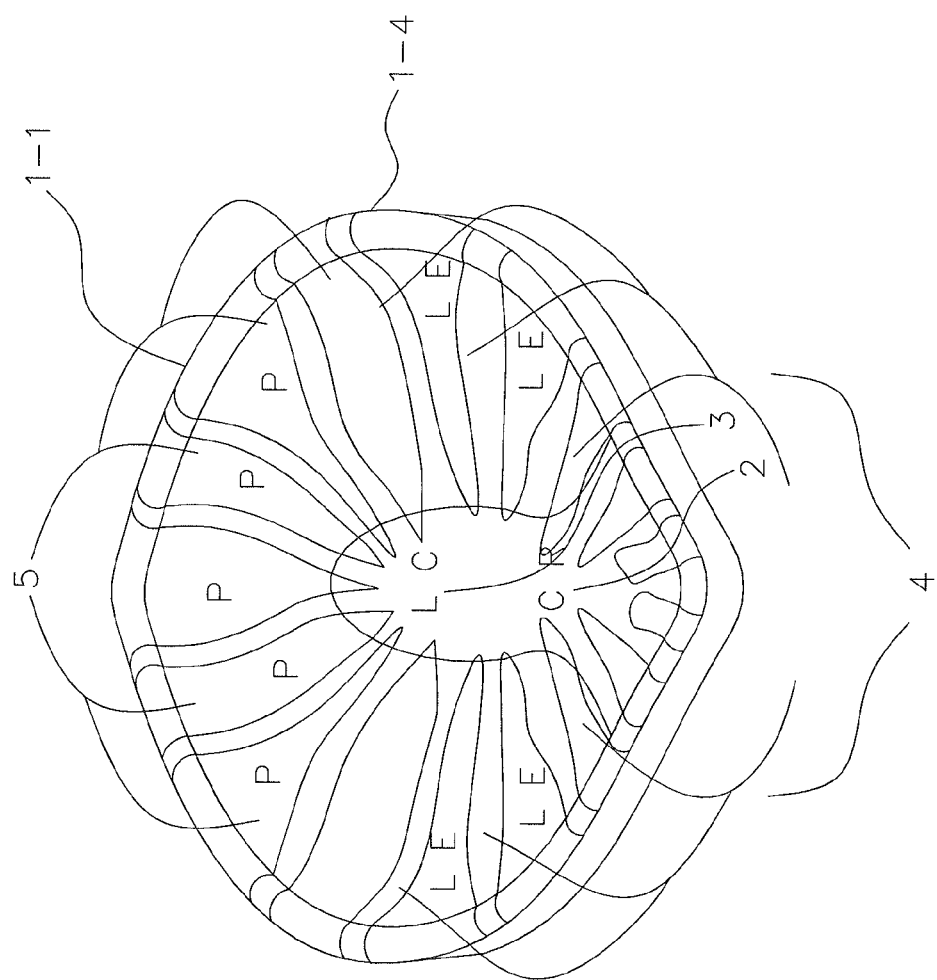
FIG. 2 is a view of the internal topography of the maxillary guidance component of the AGP showing the specific guidance of a centric relation stop, long centric area, lateral excursion guidance, and protrusive guidance.

FIG. 2 is a view of the internal topography of the maxillary guidance component (1-1) of the AGP showing the specific guidance of a centric relation stop, long centric area, lateral excursion guidance, and protrusive guidance. As shown in FIG. 2, the maxillary guidance component (1-1) of the AGP has a flat area for a stable centric relation stop, CR, (2) extended into a further area of flat for the long centric position, LC, (3) of the mandible extending laterally and anteriorly into blended inclines of a concave shape for lateral excursion guidance, LE, (4) and protrusive excursion guidance, P, (5) to provide ideal anterior guidance to the patient's mandible by the mandibular guidance component (1-2) against these features of the maxillary guidance component (1-1) to minimize muscular force and avoid all posterior interferences. This feature of appropriate anterior guidance, which moves the mandible downward (inferiorly) in its excursions, allows for a night guard of significantly less vertical dimension, VD, at rest than other designs much like an ideal occlusion would.

Figure 3:
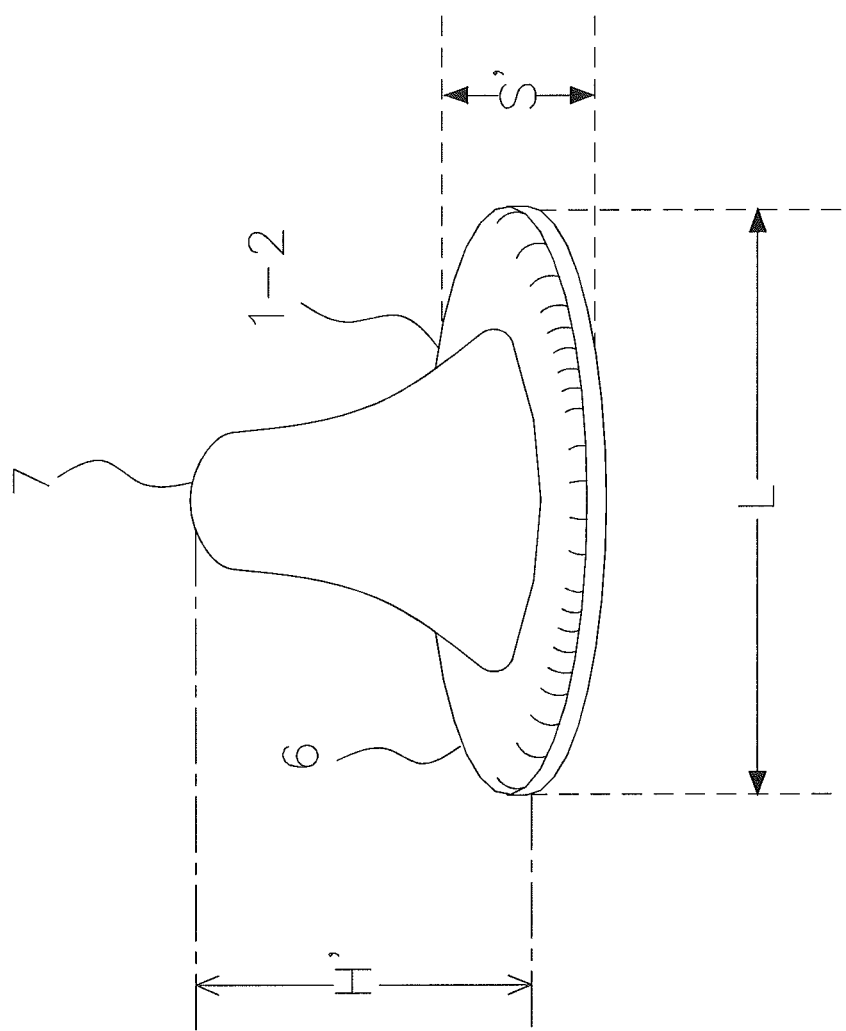
FIG. 3 is a perspective view of the mandibular guidance component of the AGP (Anterior Guidance Package).

FIG. 3 is a perspective view of the mandibular guidance component (1-2) of the AGP kit (1). The base (6) of the mandibular guidance component (1-2) has the square ovoid shape and the same dimension as the maxillary guidance component (1-1) as shown in FIG. 2.

The length of the long axis (L') of the oval shaped mandibular guidance component (1-2) is, including but not limited to, between 15 to 35 mm. And the length of the short axis (S') of the oval shaped mandibular guidance component (1-2) is, including but not limited to, between 8 to 20 mm.

A smooth rounded protrusion (7) is developed on one surface of the square ovoid shaped mandibular guidance component (1-2). Tip of the protrusion (7) is engaged in the flat to concave inner surface of the maxillary guidance component (1-1) and guides and limits the movement of a patients' mandible. Height of the smooth protrusion is, including but not limited to, between 1 to 6 mm, preferably 5 mm.

Figure 4:
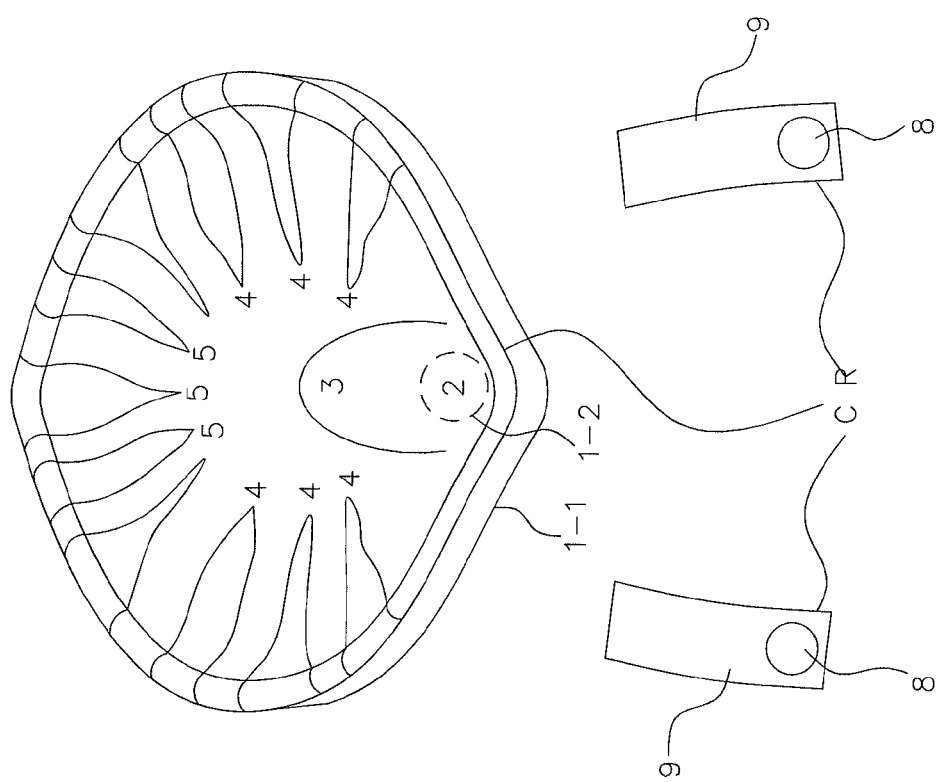
FIG. 4 is a superior transparent view of the AGP (Anterior Guidance Package) correlating the centric relation position of the TMJ's (Temporomandibular joints) coincident with the indexing of the AGP, and the available guidance to the mandibular guidance component from the maxillary guidance component from the position of centric relation.

FIG. 4 is a superior transparent view of the AGP correlating the centric relation position of the TMJs' (Temporomandibular Joints) (9) coincident with the indexing of the AGP, and the available guidance to the mandibular guidance component from the maxillary guidance component from the position of centric relation. FIG. 4 shows a superior transparent view of the AGP. It shows how the AGP of current invention replicates ideal anterior guidance as defined in current dental literature and the experience of the inventor. In FIG. 4, point (2) represents where the mandibular guidance component (1-2) sits at rest in the maxillary guidance component (1-1) when the condyle (8) of the TMJ (9) of the mandible is in its centric relation (CR) position. As a patient functions or bruxes his mandible, the mandibular guidance component (1-2) provides ideal anterior guidance for the mandible by means of the mandibular guidance component (1-2) functioning against the maxillary guidance component (1-1) in the position of centric relation (2), long centric (3), lateral excursions (4), and protrusive guidance (5). The AGP provides ideal anterior guidance without regard to the position of teeth, the condition of teeth or missing teeth.

The special retention piece (U.S. patent application Ser. No. 13/774,920), as shown in FIGS. 5-a and 5-b, eliminates any limitation of applying the AGP to any patient with any malocclusion.

FIG. 5-a is a perspective view of the special retention piece (10) to receive the AGP and FIG. 5-b is a side view thereof. The special retention piece (10) for the maxilla or mandible has a shelf (11) to receive the appropriate component of the AGP (Anterior Guidance Package). The shelf (11) is located on the most anterior aspect of the retention piece (10). Vertical position of the shelf (11) may vary from the open side (10-0) of the groove (11-1) that molds to the teeth down to the closed side (10-C) of the groove of the retention piece (10). The shelf (11) is inserted to a groove (11-1), which is vertically developed on the anterior surface of the special retention piece (10).

With the help of the special retention piece (10), the applicant has successfully created the AGP equipped special splint (night guard) for patients who have different types of malocclusion and have bruxism at the same time.

Figure 6:
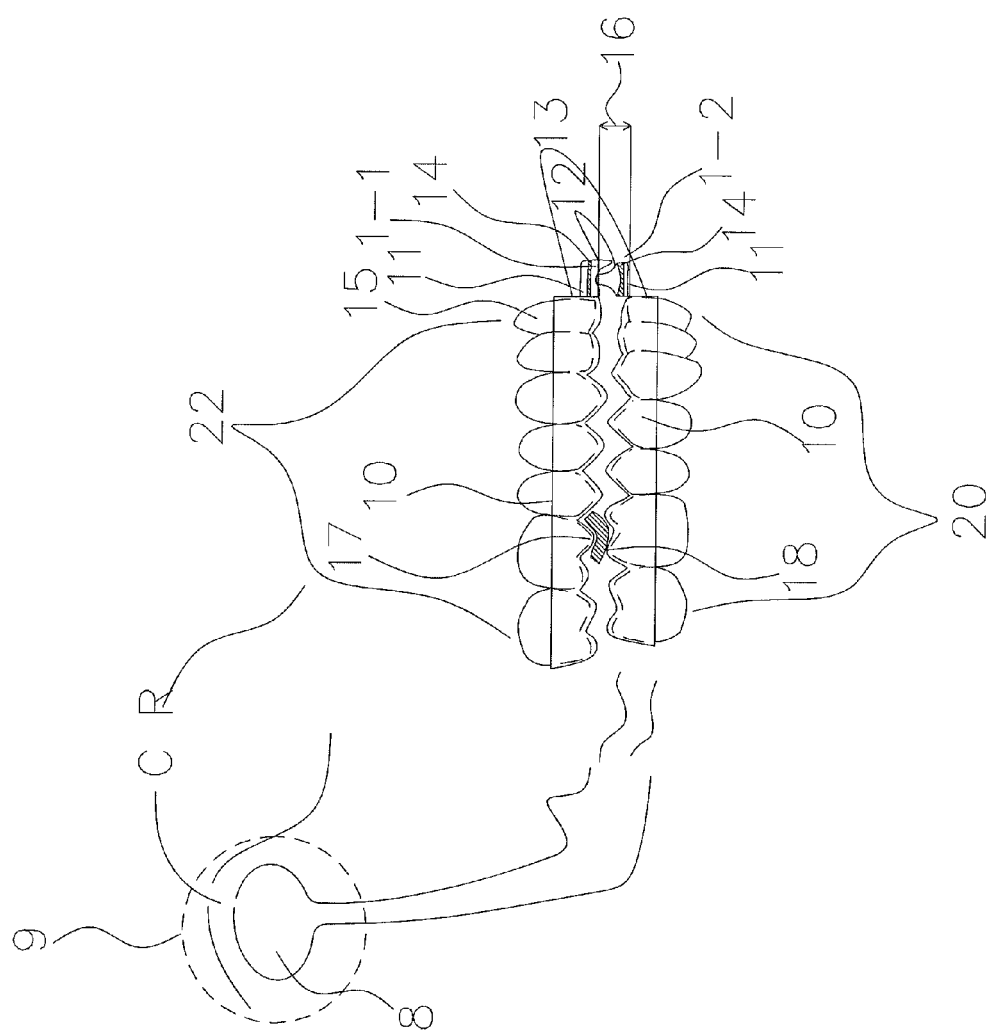
FIG. 6 is a schematic drawing that shows how to use special retention pieces of the current application as retentive pieces and platforms for the AGP for both the maxillary and mandibular arches simultaneously to allow the placement of the AGP anterior to the front teeth to comprise a special splint.

FIG. 6 is a schematic drawing that shows how to use the special retention pieces (10) as retentive pieces and platforms for the AGP for both the maxillary and mandibular arches simultaneously to allow the placement of the AGP (12) anterior to the front teeth to comprise a special splint (13). FIG. 6 is a schematic drawing that shows how the special retention piece (10) can be used for both the maxillary and mandibular retentive pieces to enable the AGP (12) to be placed anterior to the anterior teeth to comprise a splint (13) that is a combination of the special retention pieces (10) and an AGP (12). The AGP (12) is attached to the shelf (11) via glue (14). The space between the retention pieces (10) for mandibular and maxillary is exaggerated to help understand the first contact point (17) and relative interferences (or collisions) of cusps of the teeth.

One major advantage of the AGP (12) is that anterior guidance is not dependent upon teeth. One way to exploit this unique characteristic of the AGP (12) and improve the performance of a night guard, as shown in FIG. 6, is to place the AGP (12), and therefore the anterior guidance further anterior than where the anterior teeth (15) are located. This strategy can increase the mechanical advantage of the AGP (12) over the muscles of mastication in contrast to any previous system.

Another advantage over any previous night guard system that the AGP (12) has, by placing the AGP (12) further anterior than the actual position of the maxillary anterior teeth (15) would dictate, is the ability to provide anterior guidance in a splint with extremely minimal vertical dimension (16) increase when the patients mandible is at rest in centric relation. Since the AGP (12) is located ANTERIOR to the maxillary anterior teeth (15), the material required to provide the anterior guidance correction and elimination of interferences (collisions) is not in addition to that of the maxillary anterior teeth (15), but rather anterior to and independent of the maxillary anterior teeth (15), and is true anterior guidance displacing the mandible inferiorly in excursions. This minimal vertical dimension (16) at rest made possible by the AGP (12) combined with the special retentive pieces (10) increases patient's acceptance and comfort dramatically. The method of finding the first contact (17) and the use of a 1 mm sticky spacer (18) to identify and create appropriate space in centric relation (CR) is described in detail in the applicant's previous U.S. patent application Ser. No. 13/573,283.

Figure 7:
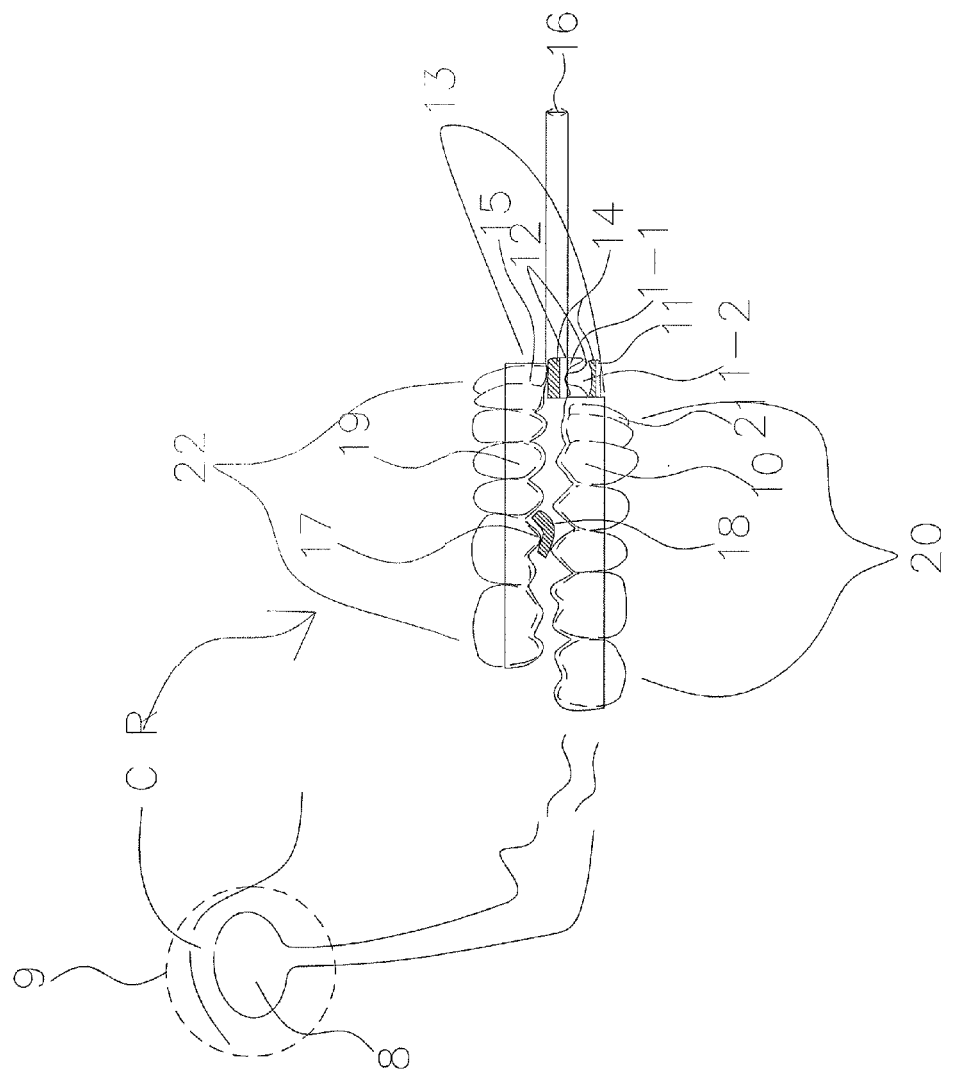
FIG. 7 is a schematic drawing that shows the use of one special retention piece of current application and one regular retention piece for a patient who presents with a significant Class II malocclusion.
Figure 8:
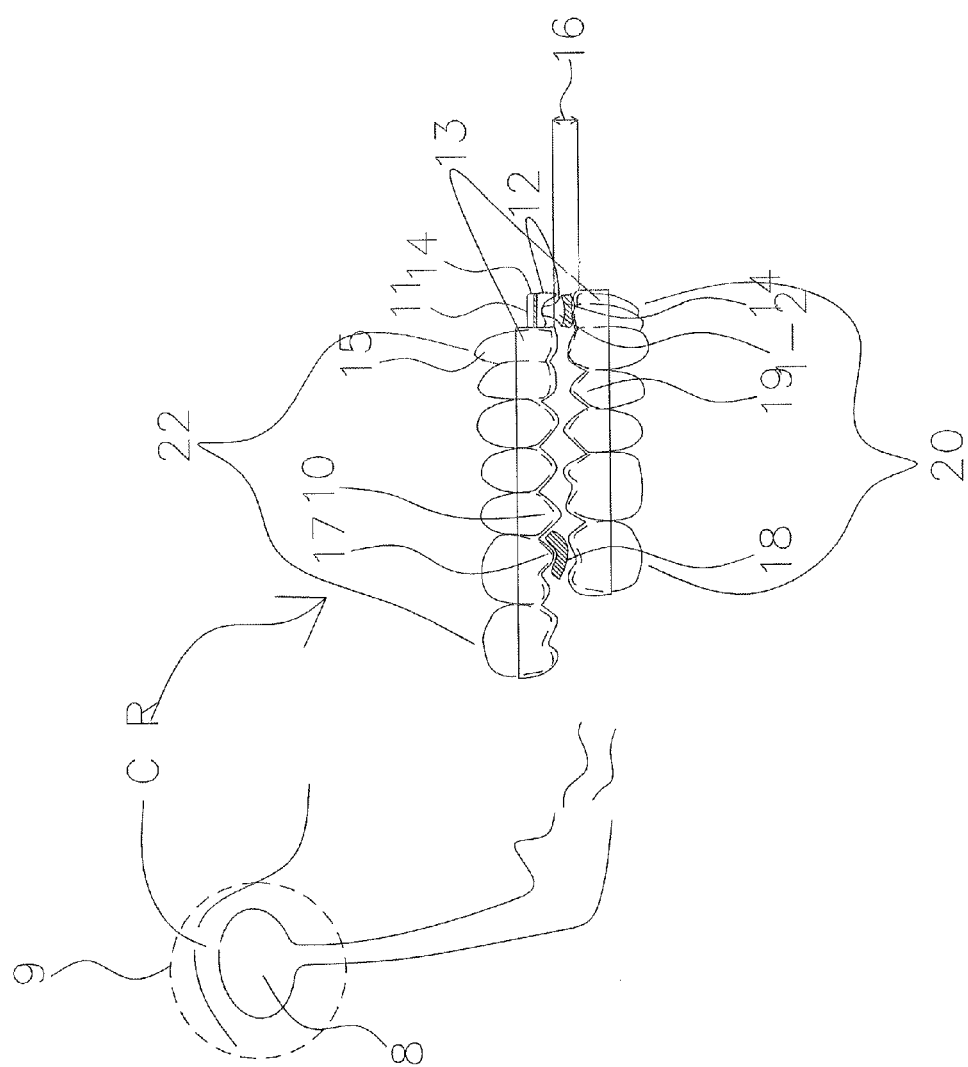
FIG. 8 is a schematic drawing that shows the use of one special retention piece of current invention and one regular retention piece for a patient who presents with a significant Class III malocclusion.

FIG. 7 and FIG. 8 are schematic drawings that show the use of one special retention piece (10) and one regular retention piece (19) for a patient who presents with a significant Class II malocclusion and with a significant Class III malocclusion, respectively.

FIG. 7 shows the use of one special retention piece (10) and one regular retention piece (19) for a patient who presents with a significant Class II malocclusion. The special retention piece (10) is used on the retrognathic mandibular arch (20) and allows placing the AGP (12) (therefore anterior guidance) anterior to the anatomical position of the mandibular front teeth (21). As shown in FIG. 7, the vertical dimension (16) of the AGP splint (13), is minimized by combining the special retention piece (10) and a regular retention piece (19). Therefore, a patient suffering significant Class II malocclusion and bruxism will have a night guard with much greater mechanical advantage and will be more comfortable than any of the previous night guard systems due to minimal vertical dimension increase at rest in centric relation. Also, a dentist can provide a proper night guard for a patient who has these problems with much less effort.

FIG. 8 shows the use of one special retention piece (10) and one regular retention piece (19) for a patient who presents with a significant Class III malocclusion. The special retention piece (10) is used on the maxillary arch (22) so the AGP can be placed anterior to the anatomical limitation of the maxillary front teeth (15). As shown in FIG. 8, the vertical dimension (16) for a patient at rest of the AGP splint (13), is minimized by combining the special retention piece (10) and a regular retention piece (19). Therefore, a patient suffering significant Class III malocclusion and bruxism will have a night guard with much greater mechanical advantage, and is more comfortable than any of the previous night guard systems, because of minimal vertical dimension increase at rest in centric relation. Also, a dentist can provide a proper night guard for a patient who has these problems with much less effort.

As described above, the AGP equipped splint has great benefit over the traditional night guard for a patient with bruxism. However, creating a customized AGP splint is time consuming and expensive for both the dentist and patient. In the event that the patient loses or damages that splint the whole process must be repeated, creating again significant expense and inconvenience to both dentist and patient.

CAD-CAM AGP Splint

To provide a method that is more convenient, that is less expensive, that is less work intensive for both the dentist and the patient, the applicant has invented a method of automatically producing or reproducing a customized AGP equipped splint.

The method of automatically producing or reproducing a customized AGP equipped splint is to combine digital methods and/or traditional methods converted to digital to collect and create information needed to automatically fabricate a specifically customized AGP equipped splint for a specific patient. And when that patient needs a new one due to loss or damage, one can be provided without visiting the dentist again. Once the dental information collected from a specific patient is stored in a computer, a new AGP equipped splint could be produced by a CNC (Computer Numerical Control) lab without any further work by the dentist or patient. Alternatively, if one or two variables regarding the patients' teeth or movement parameters have changed, these could be changed in the computer records, sent to a CNC lab, and a new AGP equipped splint could be produced without the necessity of a complete records collection session by the dentist and patient.

The procedure for the collection and creation of a patient's dental information record is as follows;

1a) Gather 3D information of maxillary and mandibular teeth using traditional methods (making impressions of the patients teeth and pour in stone to make models) and convert to digital by scanning the models, or directly record the 3D information of the maxillary and mandibular teeth with an in-office scanner. Also, collect a centric relation record at first contact using traditional methods and converting to digital by scanning the mounted models or directly record the relationship of the maxillary and mandibular teeth in centric relation at first contact using an in-office scanner. Alternatively, in the case of a TMD (Temporomandibular Joint Disorder) AGP splint, record the position at which the operator prefers to keep the patients' mandible when it is closed and at rest by scanning the models in that position or directly record that relationship between maxillary and mandibular teeth with an in-office scanner.

Figure 9:
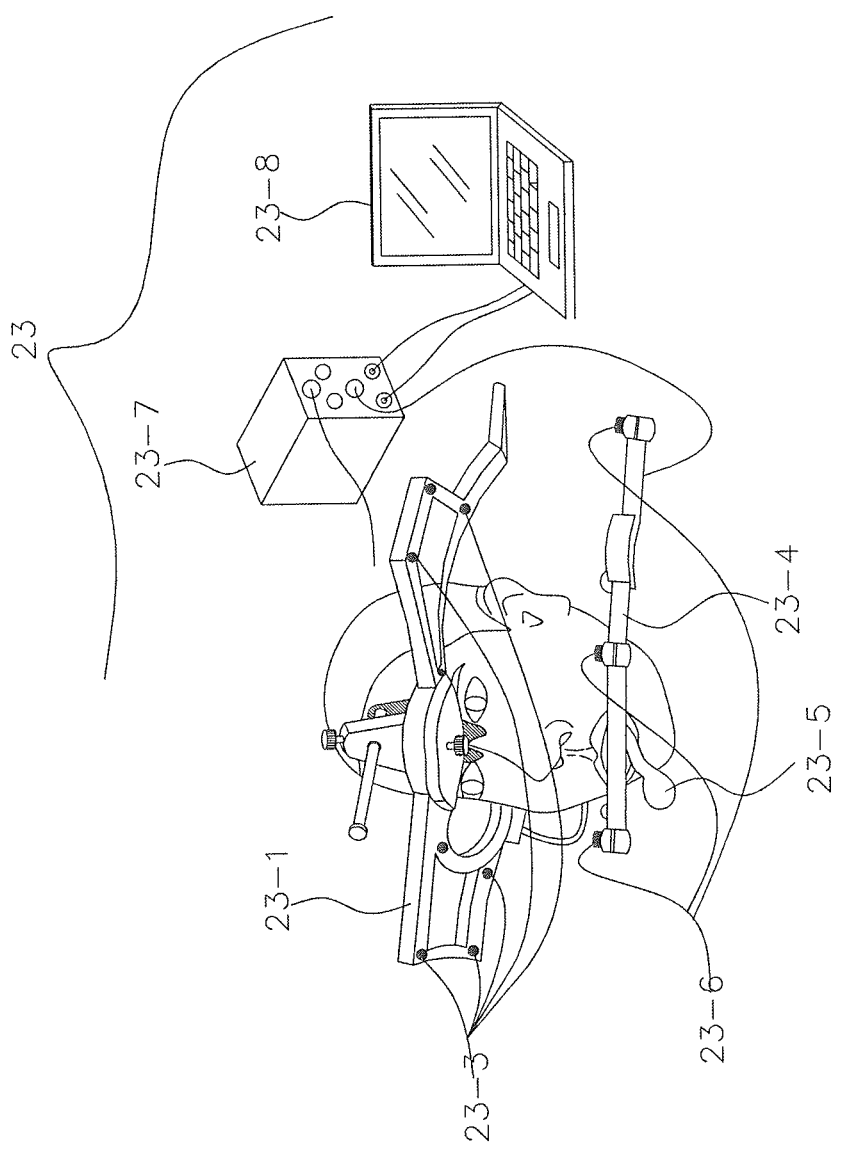
FIG. 9 is a drawing of a Jaw Motion Analyzer that enables the collection of TMJ (temporomandibular joint) data from a patient and visualization of jaw movement of a patient in real time.

1-b) Gather TMJ (Temporomandibular Joint) records using traditional methods and/or by using axiography and/or a Jaw Motion Analyzer. These records are not limited to but could include: facebow transfer, intercondylar distance, condylary inclination, Bennet angle and border limits FIG. 9 is a drawing of a Jaw Motion Analyzer system (23), which enables the collection of these data and visualization of jaw movement of a patient in real time. It comprises of an upper receiver (23-1) that is mounted on the upper face defining parameters to include the locations of the TMJ's of a patient, and is equipped with paramagnetic sensors (23-3). This unit also includes a lower receiver (23-4) that is mounted on the lower jaw of a patient, connected to the mandibular teeth of the patient via a metal splint (23-5) and another set of paramagnetic sensors (23-6) thereon, a converter (23-7) that converts the signal from the sensors (23-3), (23-6) to a computer (23-8).

2-a) Set the patients' virtual 3D maxillary and mandibular teeth in centric relation at first contact data, or the point of the operators choosing data into the virtual articulator-CAD program, which is already instored in a computer. Virtually position the digital models of the patient's maxillary and mandibular teeth on the Virtual Articulator (24) to set up a screen visualizing a Virtual Articulator (24) with patients' virtual models (25).

2-b) Set the TMJ/condylar records into the virtual articulator-CAD program, with the records collected from the patient or use average measures.

3) Virtually open the distance between the virtual models (25) along the appropriate arc of opening according to the TMJ data to an adequate distance to virtually apply the retentive piece material at a thickness of 1 mm per arch. Virtually apply the maxillary retentive piece (27) and the mandibular retentive piece (28) (Here, the retentive pieces may be different based on the malocclusion) to both arches {maxillary (22) and mandibular (20)} at a thickness of 1 mm. In this step apply the special retention piece (10) of the current application and the regular retention piece (19) separately to maxillary teeth (22) and mandibular teeth (20) based on the Class of the malocclusion of the patient as shown in the FIGS. 6, 7 and 8.

For a patient who has no severe malocclusion, Class I, special retention pieces (10) of the current invention are applied to both maxillary arch (22) and mandibular arch (20) as shown in the FIG. 6.

Figure 10:
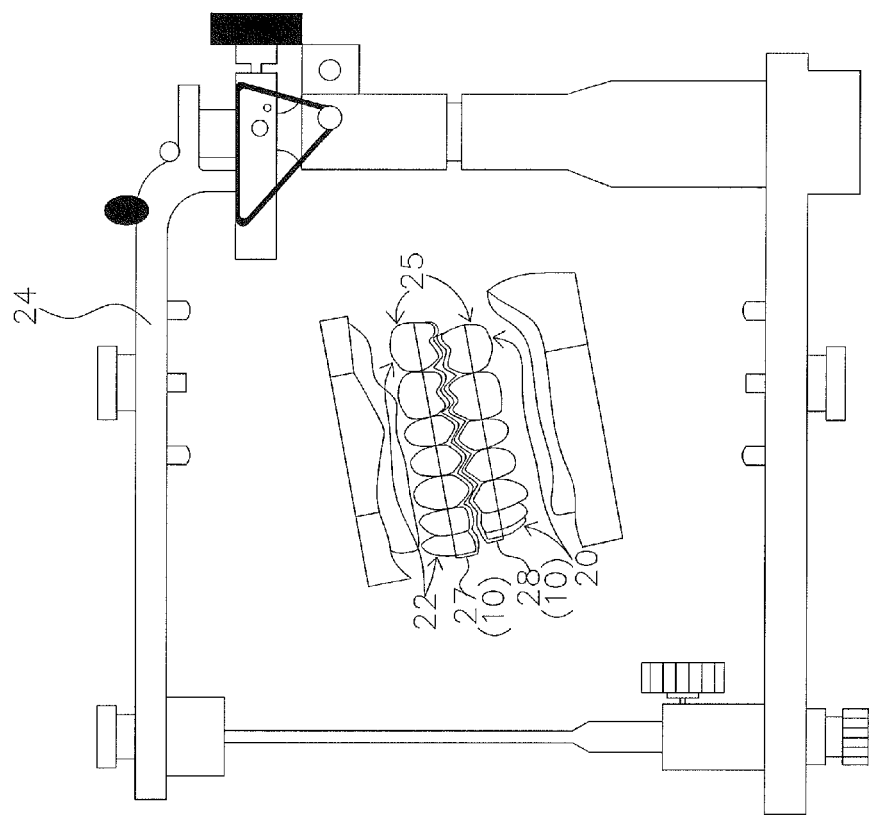
FIG. 10 is a typical computer screen of a virtual articulator when virtual models of a patient's teeth are set up based on the input data from a patient, who has a Class I occlusion, and have the virtual retention pieces in place.

FIG. 10 shows a typical computer screen of a Virtual Articulator/CAD system (24) when virtual models (25) of the patient's teeth are set up based on the input data from a patient, who has a Class I occlusion, collected from step 1-*a* and *b*) and the virtual retentive pieces have been applied to the virtual models.

4. On the Virtual Articulator (24) with the virtual retentive pieces (27), (28) in place and the jaw position beginning in virtual centric relation at first contact, animate and measure the jaw movements to include laterotrusion to all border limits of the mandible.

5. After defining the movement parameters, collision (interference) detection is required in order to identify the movement restrictions. These movement restrictions, contact points and depths are identified.

Figure 11:
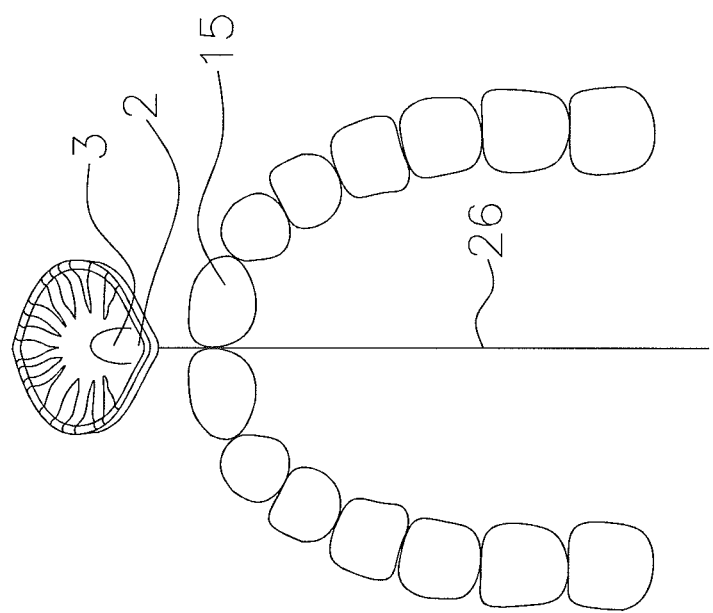
FIG. 11 is a conceptual drawing of the relative position of the AGP (on a maxillary occlusal plane mid-sagitally) to the maxillary teeth set up in the virtual environment of a virtual articulator.
Figure 12:
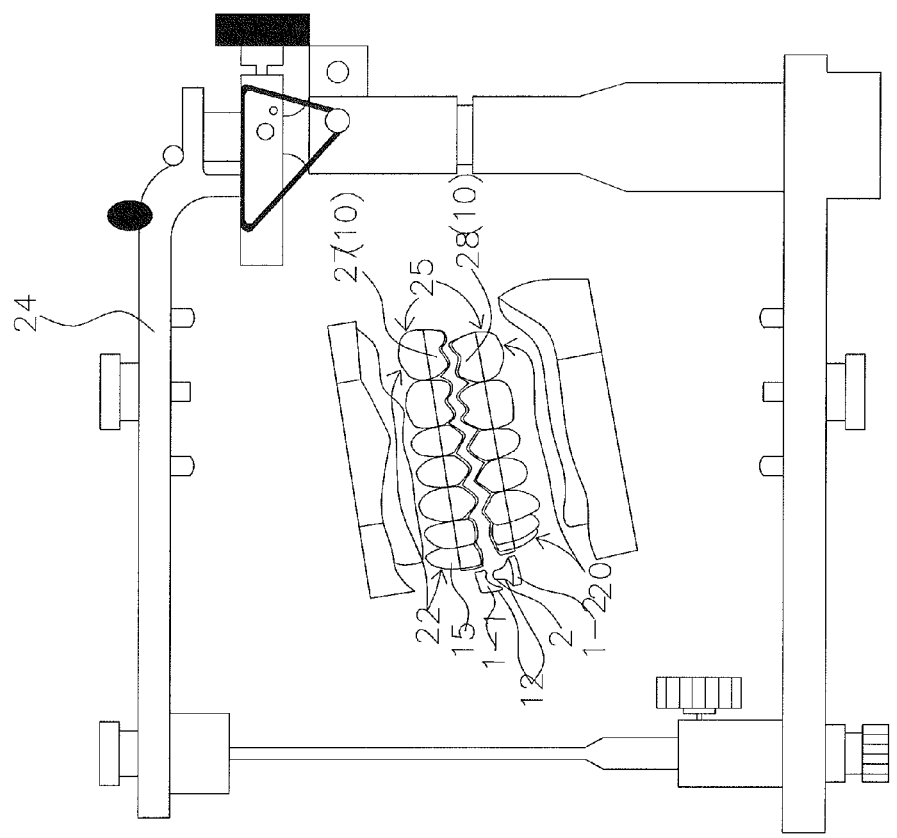
FIG. 12 is a virtual side view when the virtual AGP is placed relative to the virtual retention pieces according to the relative position in FIG. 11 in the virtual environment of a virtual articulator.

6. For a Class I occlusion, identify a point in space that is six millimeters anterior to the most anterior maxillary tooth (15), along the occlusal plane (a plane passing through the occlusal surfaces of the maxillary teeth) mid-sagitally (26). FIG. 11 is a conceptual drawing of the relative position of the virtual AGP (12) on a maxillary occlusal plane mid-sagitally (26). And FIG. 12 is a virtual side view of the AGP (12) relative to the retentive pieces (27), (28) according to the relative position in FIG. 11. At this point the operator will virtually place point (2) (see FIG. 2, FIG. 4, FIG. 11 and FIG. 12) of an AGP (12). Point (2) represents where the mandibular guidance component (1-2) sits at rest in the maxillary guidance component (1-1) when the condyles (8) of the temporo-mandibular joints (TMJ's) (9) of the mandible are in their centric relation (CR) positions (the jaw is in its virtual centric relation), developed vertically to provide 1 mm of space between the retention pieces (where they would otherwise contact). Alternatively, for instance as an example a TMD AGP splint, such as an Anterior Repositioning AGP splint, the location of Point (2) could be coincident to some position of the condyles (8) within the TMJ's (9) other than centric relation, developed vertically to provide 1 mm of space between the retention pieces (where they would otherwise contact).

Figure 14:
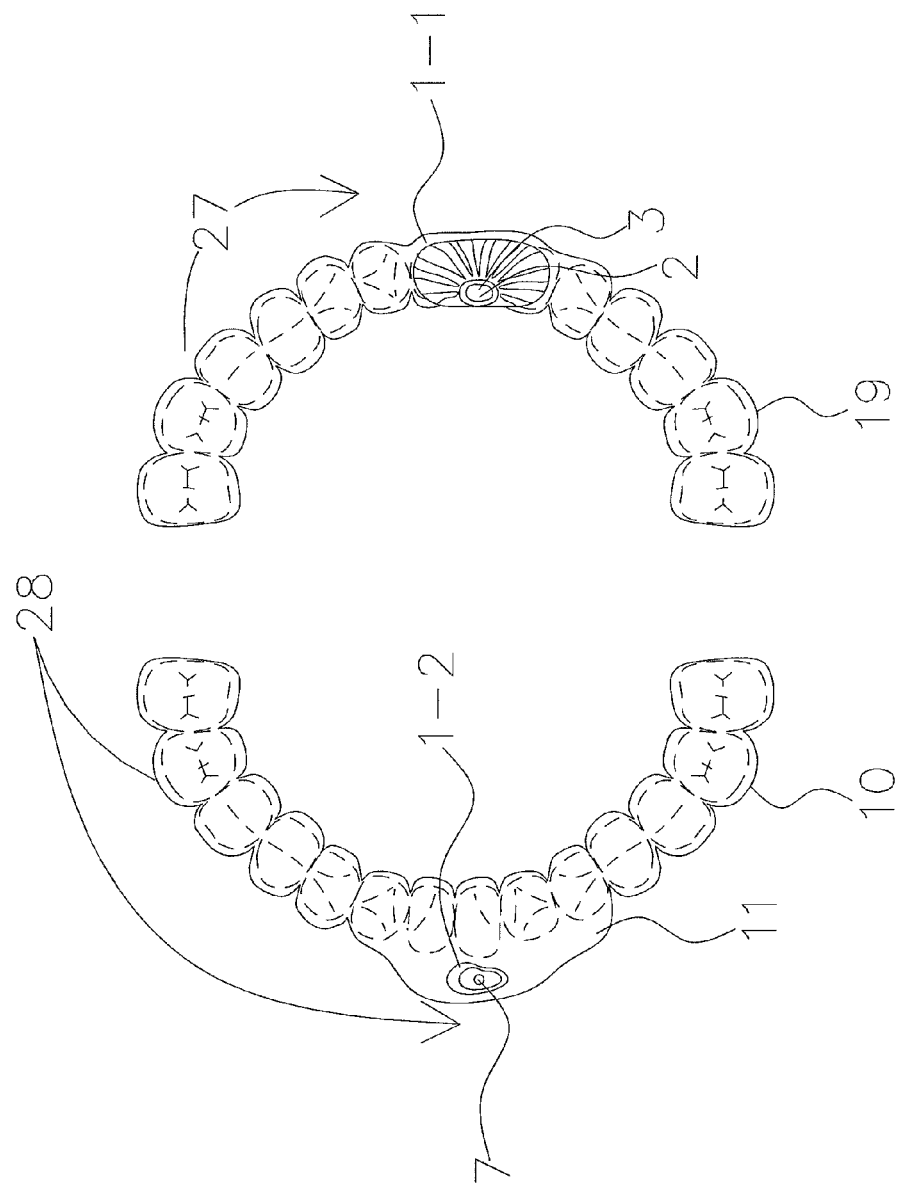
FIG. 14 is a perspective view of a completed CAD-CAM AGP splint for a patient with a Class II malocclusion from the inside of the mouth.
Figure 15:
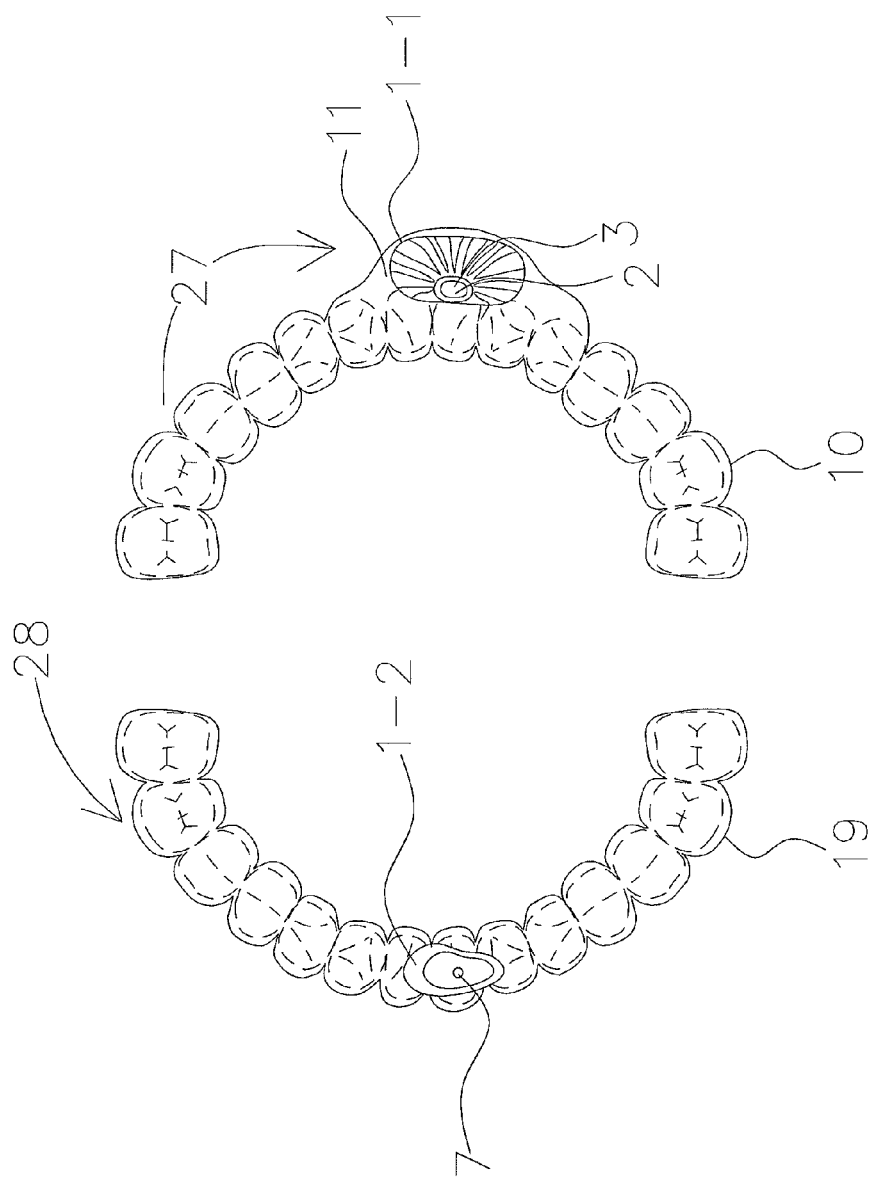
FIG. 15 is a perspective view of a completed CAD-CAM AGP splint for a patient with a Class III malocclusion from the inside of the mouth.

This point of reference for the placement of point (2) of the virtual AGP could be any of the operators choosing. For a severe Class II malocclusion patient, this point could be placed more posterior (FIG. 14). For a severe Class III patient, point (2) of the virtual AGP could be place further anterior (FIG. 15).

The operator could at this point virtually construct an AGP package of any design around Point (2) as shown in FIG. 2. All parameters of guidance can be controlled to include placement of lateral guidance (4) and protrusive guidance (5) as shown in FIG. 2. The operator may use the border limits of the mandible to define the overall size of the AGP (12). The depth (32) of the AGP, shown in FIG. 1, can be controlled. The steepness, (33), shown in FIG. 1, of the guidance can be dictated by the operator. In some cases, for instance as an example a TMD AGP splint, the guidance may be asymmetrical, or the range of motion could also be proscribed asymmetrically Alternatively, the operator could choose an AGP package from a library of stock virtual AGP package designs of different sizes and shapes. As an example, a common application would be to select a stock virtual AGP package that is large enough to guide around all interferences (collisions, movement restrictions) in a symmetrical way.

7. Once the AGP package has been virtually modeled or chosen from a library, a virtual functional simulation on the virtual articulator of the anterior guidance provided by the virtual AGP is performed to verify the operators' goals. Many options are available in treating TMD. However most commonly, the goals will be the elimination of all interferences posterior to the AGP with minimal vertical dimension increase at centric relation creating a superior anterior guidance bruxism splint.

8. Virtually apply material as a bridge between the retentive trays and the virtual AGP taking care to remain inside the envelope of function of the AGP on both the maxillary and mandibular aspects of the AGP splint. In step 6 and this step, the vertical dimension (16) for a patient at rest of the AGP splint (13) in the examples of FIG. 6 through 8 can remain minimized irrespective of the Class of the malocclusion by fixing the relative position of the virtual shelf (11) on the frontal surface of the special retentive piece (10) of the current invention that receives the appropriate component of the AGP (12). One of the unique qualities of the AGP, to enable guidance irrespective of the positions of the teeth, combined with the virtual special retentive piece and shelf, enables the operator to place the AGP package in a location to maximize guidance and minimize vertical dimension at rest. Refer to FIGS. 5-*a* and 5-*b*. As shown in FIG. 7 and FIG. 8 the shelf (11) receives the mandibular guidance component (1-2) of the AGP (12) for a Class II malocclusion patient and receives the maxillary guidance component (1-1) of the AGP (12) for a Class III malocclusion patient. For a non-malocclusion case, Class I, FIG. 6, the special retentive piece (10) of the current invention may be applied as a bridge to the AGP for both the maxillary arch (22) and mandibular arch (20).

9. This data and information, collected from the above steps, is transferred to a manufacturer who has CAM (Computer Aided Manufacturing) or CNC technology and equipment. A two-piece CAD-CAM AGP splint can now be automatically produced or re-produced that is customized for a specific patient, consisting of a maxillary aspect and a mandibular aspect, which is comfortable to wear, irrespective of the malocclusion type including open bite, deep bite, cross bite, severe Class II, and Class III. Refer FIGS. 6 to 8, whenever needed.

Figure 13:
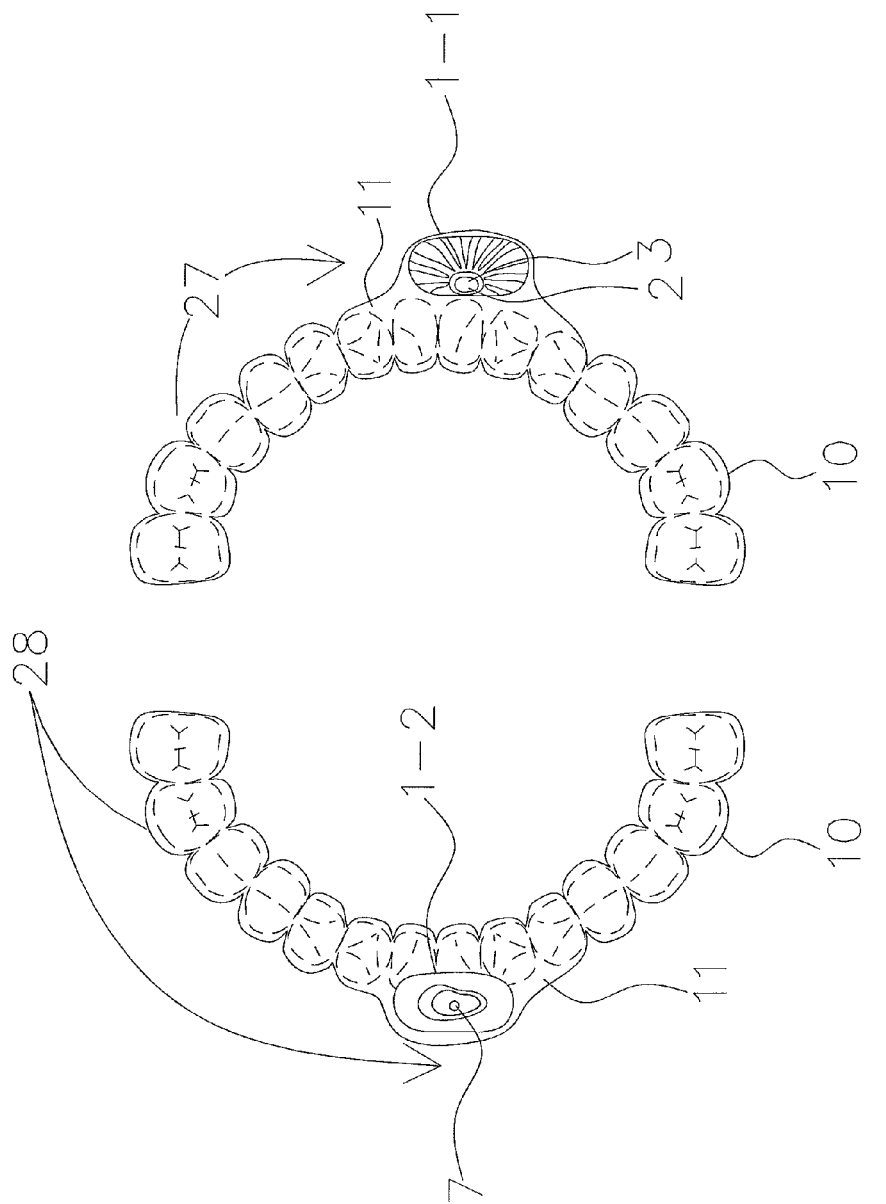
FIG. 13 is a perspective view of a completed CAD-CAM AGP splint for a patient without a severe malocclusion, Class I, from the inside of the mouth.

FIG. 13 is a perspective view of a completed CAD-CAM AGP splint for a patient without a severe malocclusion, Class I, from the inside of the mouth. In this case both the maxillary retentive piece (27) and mandibular retentive piece (28) of the CAD-CAM AGP splint will be comprised of the special retentive pieces (10) of the current invention. Both the maxillary and mandibular AGP splint components, including in each case the retentive piece and the guidance portion (1-1), or (1-2) of the AGP, may be connected seamlessly.

FIG. 14 is a perspective view of a completed CAD-CAM AGP splint for a patient with a severe Class II malocclusion from inside the mouth. So, for a severe Class II malocclusion the mandibular retention piece (28) is a special retention piece (10) according to current application, which has a shelf (11) to receive the mandibular guidance component (1-2), and the maxillary retention piece can be a regular retention piece (19), which does not have a shelf (11) on the anterior surface.

FIG. 15 is a perspective view of a completed CAD-CAM AGP splint for a patient with a Class III malocclusion from inside the mouth. For a Class III malocclusion the maxillary retention piece (27) is a special retention piece (10) according to current application, which has a shelf (11) to receive the maxillary guidance component (1-1), and the mandibular retention piece can be a regular retention piece (19).

Located in the mouth with a minimal vertical dimension (16) penalty at rest in centric relation, or any position of the operators choosing, are thin custom-fitting retentive pieces. The AGP (12) portion of the splint (13) is located in a smooth compartment-like package between the patients' lips anterior to the teeth in most cases dependent upon the malocclusion and therefore the position of the AGP in relation to teeth and lips. As the patient closes their mouth, the maxillary component of the AGP splint will contact the mandibular component guiding the mandible into Point 2 and area 3, FIGS. 13 to 15, which is shown in more detail in FIG. 2 and FIG. 4. This area would most commonly be centric relation (Point 2 FIG. 2) and the long centric area (Area 3 FIG. 2) but could in the case of a TMD management splint, be a position other than centric relation proscribed by the operator. The maxillary component (1-1) of the AGP will fit over the mandibular component (1-2). The entire inferior perimeter of the maxillary aspect of the AGP will be wider than the mandibular aspect of the AGP and its housing. That perimeter (1-4) in FIG. 2 will also have a 2 to 6 mm thickness and shaped like a bumper to prevent the lips from ever being pinched when the patients' mouth closes.

11. Finally, when the various AGP splints (FIGS. 16 to 18), for patients with different malocclusions, are manufactured by the CAD-CAM method, all the retention pieces (27), (28) and their respective AGP components (1-1), or (1-2) are produced in one piece without any seam lines.

Figure 16:
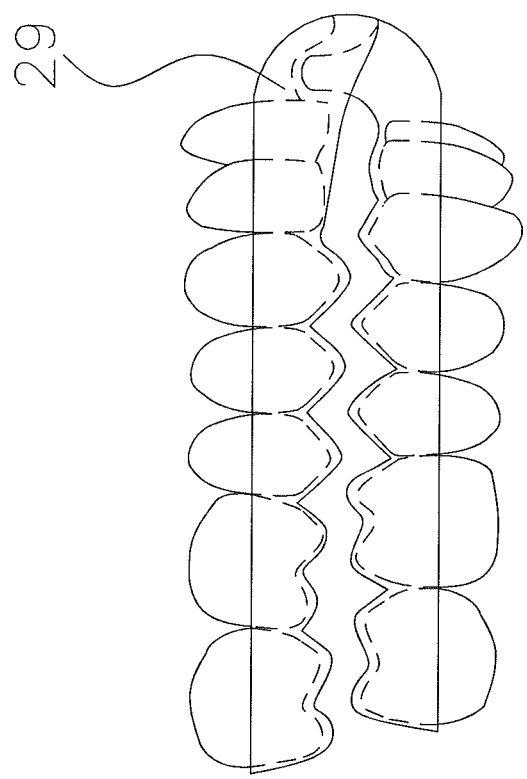
FIG. 16 is a schematic side view of a finished CAD-CAM AGP splint for a bruxism patient without a severe malocclusion, Class I.

FIG. 16 is a schematic side view of a finished CAD-CAM AGP splint (29), which may have special properties to manage a TMD patient, or a CAD-CAM AGP splint for a bruxism patient without a severe malocclusion. Compared with FIG. 6, it is simpler to produce and much simpler to reproduce.

Figure 17:
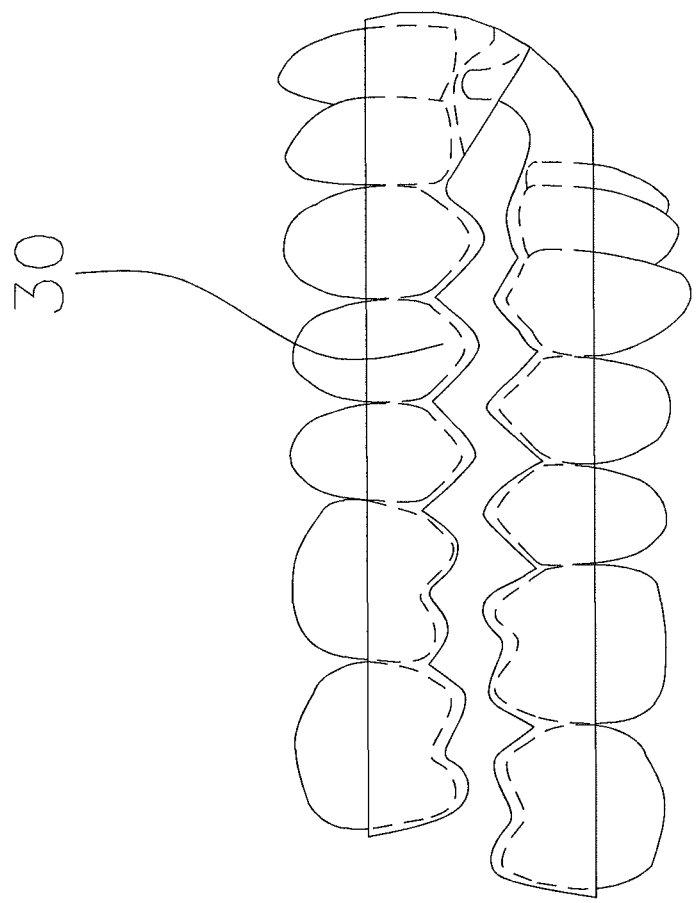
FIG. 17 is a schematic side view of a finished CAD-CAM AGP splint for a bruxism patient with a Class II malocclusion.
Figure 18:
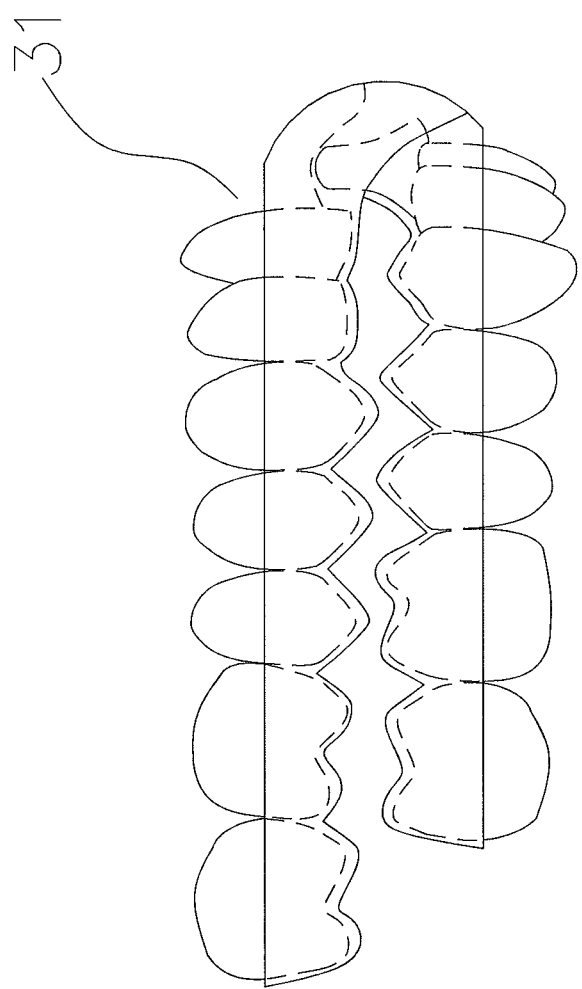
FIG. 18 is a schematic side view of a finished CAD-CAM AGP splint for a bruxism patient with a Class III malocclusion.

Similarly, FIG. 17 is a schematic side view of a finished CAD-CAM AGP splint (30) for a bruxism patient with Class II malocclusion. And FIG. 18 is a CAD-CAM AGP splint (31) for a bruxism patient with Class III malocclusion.

Since all necessary information for each patients' AGP splint is already stored in a CAM computer, the sophisticated procedure disclosed in FIGS. 6 to 8 is not necessary for a patient and dentist to reproduce the same customized AGP splint again.

The method described above can be applied to a wide range of stock AGPs, and/or a custom designed AGP for a specific patient. The AGP could have any size or shape to address a very wide range of problems or malocclusions. The maxillary component and/or the mandibular component of the AGP can be designed or modified to any shape or size either individually or as a group to achieve whatever effect the operator desires. For instance, a TMD (TemporoMandibularDisorders) therapist will have available to her/him an unprecedented range of options regarding both limits and guidance to the mandible. In contrast to other systems, the AGP can provide unlimited true anterior guidance, and limits to the mandible independent of the condition, position, presence or absence of teeth. Also uniquely attributable to the AGP, the position of the AGP (and therefore guidance and limits of the mandible) within the AGP splint can be controlled to maximize or minimize different properties of the AGP splint. Considering the unlimited design potential of the AGP, and the extreme flexibility regarding the position of the AGP within the AGP splint, the AGP CAD-CAM splint, and the AGP CAD-CAM TMD splint are far superior to any night guard or TMD appliance system in existence today.

The CAD-CAM AGP splint is comfortable to wear, seamless, light-weight, and of minimal vertical dimension at rest in centric relation (or a different position of the operators choosing) because of one of the distinct advantages of the AGP; the ability to place true anterior guidance anterior to the teeth and therefore not in between the teeth. The CAD-CAM AGP splint features superior anterior guidance compared to anything existing in the marketplace today. This is because the guidance is located even further anterior to the muscles of mastication and therefore has inherent superior mechanical advantage as compared to any guidance involving teeth. In contrast to any previous night guard or TMD treatment system, the CAD-CAM AGP splint has unlimited flexibility in the design of the anterior guidance. In contrast to any previous night guard or TMD treatment system, the CAD-CAM AGP splint can be produced without regard or concern as to the condition, presence or absence of anterior teeth.

In the event the patients' CAD-CAM AGP splint is lost or destroyed, a digital record exists to recreate a duplicate appliance quickly, without the need of a new record making appointment. A new CAD-CAM AGP splint replacement can be provided conveniently, and with cost savings for the patient.

The CAD-CAM AGP splint can be produced less expensively than traditional methods of the dentist and his lab manually producing and adjusting a splint. The CAD-CAM AGP splint is a superior splint for addressing both TMD issues, and bruxism. The CAD-CAM AGP splint in contrast to all existing systems will provide a superior system to the patient, with greater convenience for the patient, and at a better price.

What is claimed is:

1. A method of preparing a customized Anterior Guidance Package (AGP) equipped splint for a patient using a computing device, the method comprising:
receiving patient data comprising three-dimensional maxillary and mandibular arch data and first contact point data associated with the patient, the first contact point data associated with temporo-mandibular joint (TMJ) data for visualization of jaw movement of the patient;
receiving TMJ data;
generating, using one or more processors of the computing device, one or more digital models in a virtual articulator based on the patient data, the one or more digital models comprising virtual maxillary and mandibular arches;
positioning, in the virtual articulator, the virtual arches in a predetermined index position based on the TMJ data, the predetermined index position providing a threshold clearance between the virtual arches;
applying, in the virtual articulator, a virtual maxillary retentive member to the virtual maxillary arch and a virtual mandibular retentive member to the virtual mandibular arch;
determining, based on the positioned virtual arches, a virtual maxillary attachment point for attaching a virtual maxillary guidance component to the virtual maxillary retentive member and a virtual mandibular attachment point for attaching a virtual mandibular guidance component to the virtual mandibular retentive member;
attaching, in the virtual articulator, the virtual maxillary and mandibular guidance components to their respective virtual retentive member based on the determination to form a virtual AGP equipped splint; and
transmitting AGP equipped splint production data based on the virtual AGP equipped splint.

2. The method of claim 1, wherein one or more of the virtual maxillary and mandibular attachment points is positioned anteriorly beyond a respective virtual retentive member.

3. The method of claim 2, wherein the virtual mandibular retentive member comprises a shelf extending anteriorly beyond the virtual mandibular retentive member, and attaching the virtual mandibular guidance component to the virtual mandibular retentive member comprises attaching the virtual mandibular guidance component to the shelf.

4. The method of claim 3, wherein attaching the virtual maxillary guidance component to the virtual maxillary retentive member comprises attaching the virtual maxillary guidance component to a bottom surface of the virtual maxillary retentive member.

5. The method of claim 2, wherein the virtual maxillary retentive member comprises a shelf extending anteriorly beyond the virtual maxillary retentive member, and attaching the virtual maxillary guidance component to the virtual maxillary retentive member comprises attaching the virtual maxillary guidance component to the shelf.

6. The method of claim 5, wherein attaching the virtual mandibular guidance component to the virtual mandibular retentive member comprises attaching the virtual mandibular guidance component to an upper surface of the virtual mandibular retentive member.

7. The method of claim 1, wherein the virtual guidance components, when attached to the virtual retentive members, are configured to contact one another proximate a reference plane positioned anterior to at least one of the virtual retentive members.

8. The method of claim 1, wherein the virtual mandibular retentive member comprises a protrusion having an apex, the protrusion forming the mandibular guidance component.

9. The method of claim 8, wherein the virtual maxillary retentive member comprises a concave surface configured to receive the protrusion of the virtual mandibular retentive member, the concave surface forming the virtual maxillary guidance component.

10. The method of claim 9, wherein the virtual maxillary retentive member further comprises a bumper-shaped ridge surrounding the concave surface, the ridge having a thickness between 2 mm and 6 mm.

11. The method of claim 1, wherein receiving the three dimensional maxillary and mandibular arch data further comprises collecting the three dimensional maxillary and mandibular arch data with a scanner.

12. The method of claim 1, wherein receiving the TMJ data comprises collecting TMJ data with one or more of axiography and a jaw motion analyzer, the collected TMJ data being associated with the patient.

13. The method of claim 1, wherein receiving the TMJ data comprises receiving average TMJ data associated with a plurality of patients.

14. The method of claim 1, wherein the virtual retentive members have a thickness of 1 mm.

15. The method of claim 1, further comprising producing a physical AGP equipped splint based on the virtual AGP equipped splint production data.

16. The method of claim 15, wherein producing the physical AGP equipped splint comprises computer aided manufacturing the physical AGP equipped splint as a single integrated part based on the virtual AGP equipped splint production data.

* * * * *